United States Patent
Quinn et al.

[11] Patent Number: 5,971,946
[45] Date of Patent: Oct. 26, 1999

[54] ANKLE SUPPORT BRACE

[75] Inventors: Patrick J. Quinn, Eagan; Gregory A. Hoistad, Bloomington, both of Minn.

[73] Assignee: Swede-O, Inc., North Branch, Minn.

[21] Appl. No.: 08/889,995

[22] Filed: Jul. 10, 1997

[51] Int. Cl.⁶ .................................................. A61F 5/00
[52] U.S. Cl. ............................................................ 602/27
[58] Field of Search ................................ 602/27–29, 65, 602/5–8; 128/882

[56] References Cited

U.S. PATENT DOCUMENTS

| | | |
|---|---|---|
| Re. 15,446 | 9/1922 | Hamilton . |
| Re. 33,395 | 10/1990 | Peters . |
| 112,952 | 3/1871 | Niswander . |
| 130,639 | 8/1872 | Howe . |
| 297,368 | 4/1884 | Fisher . |
| 830,894 | 9/1906 | Garrod . |
| 2,450,862 | 10/1948 | Wilkinson . |
| 3,073,305 | 1/1963 | Biggs, Jr. et al. . |
| 3,506,000 | 4/1970 | Baker . |
| 3,584,622 | 6/1971 | Domenico . |
| 3,674,023 | 7/1972 | Mann . |
| 3,780,537 | 12/1973 | Spencer . |
| 3,955,565 | 5/1976 | Johnson, Jr. . |
| 4,055,188 | 10/1977 | Pelton . |
| 4,133,311 | 1/1979 | Karczewski . |
| 4,166,460 | 9/1979 | Applegate . |
| 4,280,488 | 7/1981 | Polsky et al. . |
| 4,280,489 | 7/1981 | Johnson, Jr. . |
| 4,287,920 | 9/1981 | Johnson, Jr. . |
| 4,320,748 | 3/1982 | Racette et al. . |
| 4,378,793 | 4/1983 | Mauldin et al. . |
| 4,409,976 | 10/1983 | Pence . |
| 4,433,682 | 2/1984 | Badra . |
| 4,510,927 | 4/1985 | Peters . |
| 4,556,054 | 12/1985 | Paulseth . |
| 4,577,419 | 3/1986 | Chassaing . |
| 4,587,962 | 5/1986 | Greene et al. . |
| 4,590,932 | 5/1986 | Wilkerson . |
| 4,628,945 | 12/1986 | Johnson, Jr. . |
| 4,665,904 | 5/1987 | Lerman . |
| 4,693,239 | 9/1987 | Clover, Jr. . |
| 4,844,094 | 7/1989 | Grim . |
| 4,865,023 | 9/1989 | Craythorne et al. . |
| 4,905,998 | 3/1990 | Last . |
| 5,007,416 | 4/1991 | Burns et al. . |
| 5,031,607 | 7/1991 | Peters . |
| 5,038,762 | 8/1991 | Hess et al. . |
| 5,209,722 | 5/1993 | Miklaus et al. . |
| 5,226,875 | 7/1993 | Johnson ..................................... 602/27 |
| 5,366,439 | 11/1994 | Peters ....................................... 602/27 |
| 5,716,335 | 2/1998 | Iglesias et al. ............................ 602/27 |

FOREIGN PATENT DOCUMENTS

WO 88/09156  12/1988  WIPO .

OTHER PUBLICATIONS

"Ankle Joint Support: A Comparison of Reusable Lace-on Braces With Taping and Wrapping", Bunch, et al., *The Physician and Sports Medicine*, vol. 13, No. 5, May 1995 (4 pp.).

(List continued on next page.)

*Primary Examiner*—Linda C. M. Dvorak
*Attorney, Agent, or Firm*—Merchant, Gould, Smith, Edell, Welter & Schmidt

[57] ABSTRACT

A preferred embodiment ankle brace includes a foot plate and opposing uprights extending upward from opposite sides of the foot plate. Cleats protrude downward from the bottom of the foot plate. The ends of the junctions between the uprights and the foot plate curve outside the planes defined by the respective uprights and the foot plate. The foot plate and uprights are symmetrical about a plane of symmetry which extends perpendicularly between the opposite sides of the foot plate. A lateral side panel is rotatably connected to one upright, and a medial side panel is rotatably connected to the other upright at a relatively greater distance away from the foot plate. Flat, oval-shaped bearing surfaces are disposed on abutting sides of respective uprights and side panels. Pads are secured within the side panels and ventilation channels and holes are formed in the pads.

21 Claims, 7 Drawing Sheets

OTHER PUBLICATIONS

"The Effects of the Swede–O, New Cross, and McDavid Ankle Braces and Adhesive Ankle Taping on Speed, Balance, Agility, and Vertical Jump", Paris, *Journal of Athletic Training*, vol. 27, No. 3, 1992, pp. 253–256.

"High– versus low–top shoes for the prevention of ankle sprains in basketball players", Barrett, et al., *American Journal of Sports Medicine*, vol. 21, No. 4, 1993, pp. 582–585.

"Isometric Strength of Rearfoot Inversion and Eversion in Nonsupported, Taped, and Braced Ankles Assessed by Hand–Held Dynamometer", Paris, et al., *JOSPT*, vol. 15, No. 5, May 1992, pp. 229–235.

"Retrospective comparison of taping and ankle stabilizers in preventing ankle injuries", Rovere, et al., *American Journal of Sports Medicine*, vol. 16, No. 3, 1988, pp. 228–233.

Active Ankle brochure, "We want you to throw your weight around", (2 pp.).

"The Achiever Ankle Brace" by Arthrogo brochure (4 pp.).

Ada Brace advertisement (1 p.).

Aircast advertisement (1 pg.).

Ankle Braces advertisement (1pg.).

Duo–Loc by Omni Scientific, Inc. advertisement (2 pp.).

Joint Solutions advertisement, *NATA News*, Nov. 1996 (1 pg.).

Kallassy Ankle Support by Sports Supports advertisement, (1 pg.).

McDavid "The Guardian Ankle"advertisement, *Medco Supply Company*, New Products pg.7.

Mueller No. 1 Ankle Protection "Lite Ankle Brace" and Tulis "Cheetah Ankle Brace" advertisement, 1 p.

Omni Scientific, Inc. "Phase" and "Multi Phase" advertisement brochure, 2 pp.

Three–D Foot and Ankle Systems advertisement (1 pg.)

*Official Gazette* publication of U.S Patent No.4,727,863 to R. Nelson.

*Official Gazette* publication of U.S Patent No.4,724,847 to R. Nelson, Feb. 16, 1988, pg. 1012–1013.

*Official Gazette* publication of U.S Patent No.4,719,926 to R. Nelson.

Front page of U.S. Patent No.4,649,939 dated Mar. 17, 1987 to Curtis.

Front page of U.S. Patent 4,646,726 dated Mar. 3, 1987 to Westin et al.

Front page of U.S. Patent 4,638,794 dated Jan. 27, 1987 to Grisar.

*Official Gazette* publication of U.S Patent No.4,572,169 to Mauldin et al.

*Official Gazette* publication of U.S Patent No.4,547,981 to Thais et al., Oct. 22, 1985.

*Official Gazette* publication of U.S Patent No.4,517,968 to Greene et al., May 21, 1985, pp. 1091–1092.

ANKLE SUPPORT BRACE

FIELD OF THE INVENTION

The present invention relates to supports for body members and, more particularly, to a reusable and reversible support or brace for a person's ankle.

BACKGROUND OF THE INVENTION

The human ankle consists of three bones, the tibia, the fibula, and the talus, which are bound to the bones of the foot and to one another by ligaments. The particular arrangement of the three bones allows the foot to rotate about three orthogonal axes relative to the leg. The ligaments place elastic limits on the extent of such rotation or movement.

Many ankle injuries occur when ankle movement exceeds the elastic limit of one or more ligaments. One relatively common ankle injury, known as eversion of the ankle, results when the ankle moves too far outward as the foot rolls over. Another relatively common ankle injury, known as inversion of the ankle, results when the ankle moves too far inward as the foot rolls over. Many individuals, and athletes in particular, require external support for their ankles as a result of previous eversion or inversion injuries or ongoing concerns about adequately protecting their ankles.

A common practice among athletes is to tightly wrap the ankles with medical adhesive tape. Although "taping" is generally recognized as an effective way to protect a weak or injured ankle, it suffers several drawbacks, as well. For example, an effective tape job necessarily restricts movement of the foot in all directions relative to the leg, thereby limiting desirable ankle motions as well as undesirable ones. Taping is also relatively costly because the tape is typically used only once, and it often requires a trainer to be properly applied.

Fabric ankle wraps are sometimes used as an alternative to taping. The fabric wraps may be used more than once, but their elasticity and lack of adhesiveness renders them less effective than medical adhesive tape in terms of immobilizing the joint.

A variety of relatively rigid support structures have been designed as alternatives to medical tape and fabric wraps. However, those skilled in the art continue to seek improvements in areas such as reliable support, user comfort, user mobility, application simplicity, and/or manufacturing cost.

SUMMARY OF THE INVENTION

The present invention provides an improved ankle brace of the type which includes a foot plate configured to underlie a person's foot, and uprights configured to extend upward from opposite sides of the foot plate and along opposite sides of the person's ankle.

According to one aspect of the invention, the uprights are integrally joined to the foot plate, and the ends of these integral junctures curve outward and away from the interior angle defined therebetween. The curved ends of the junctures significantly enhance the structural integrity of the improved ankle brace, providing relatively greater resistance to deflection of the uprights relative to the foot plate. The curved ends of the junctures also tend to conform to the exterior of a person's foot and the interior of a person's shoe, thereby positively contributing to foot support and overall user comfort. In a preferred embodiment, the lateral side has a longer length and substantially increases the surface area below the pivot point which results in increased positive contact with the upright and therefore significantly decreases the possibility of the side panel bending out which increases lateral support and inversion restriction.

According to another aspect of the invention, the foot plate and uprights are symmetrical about a plane of symmetry which extends perpendicularly through the lateral and medial sides of the foot plate. As a result, the improved ankle brace is not only reusable, but it is also reversible. In addition to being reversible, the foot plate has a relatively longer lateral side and a relatively shorter medial side, which contribute to foot support and user comfort. Also, a lateral side panel is rotatably mounted to the lateral upright, and a medial side panel is rotatably mounted to the medial upright at a relatively higher position above the foot plate, thereby contributing to the ergonomic fit of the improved ankle brace.

According to yet another aspect of the invention, flat, oval-shaped bearing surfaces are disposed on respective inwardly facing sides of the uprights and outwardly facing sides of the side panels, to improve ankle support without unnecessarily limiting forward and rearward tilting of the person's foot relative to the person's leg.

According to still another aspect of the invention, nubs or cleats protrude downward from the foot plate, to discourage movement of the foot plate relative to the sole of a shoe. When subjected to the weight of the user, the cleats effectively connect the foot plate to the shoe so that the shoe, the brace, and the ankle tend to move together or not at all. These and other advantages of the present invention may become more apparent from the detailed description of the preferred embodiment which follows.

BRIEF DESCRIPTION OF THE FIGURES OF THE DRAWING

With reference to the Figures of the Drawing, wherein like numerals represent like parts and assemblies throughout the several views.

DETAILED DESCRIPTION OF THE PREFERRED EMBODIMENT

Figure 1:
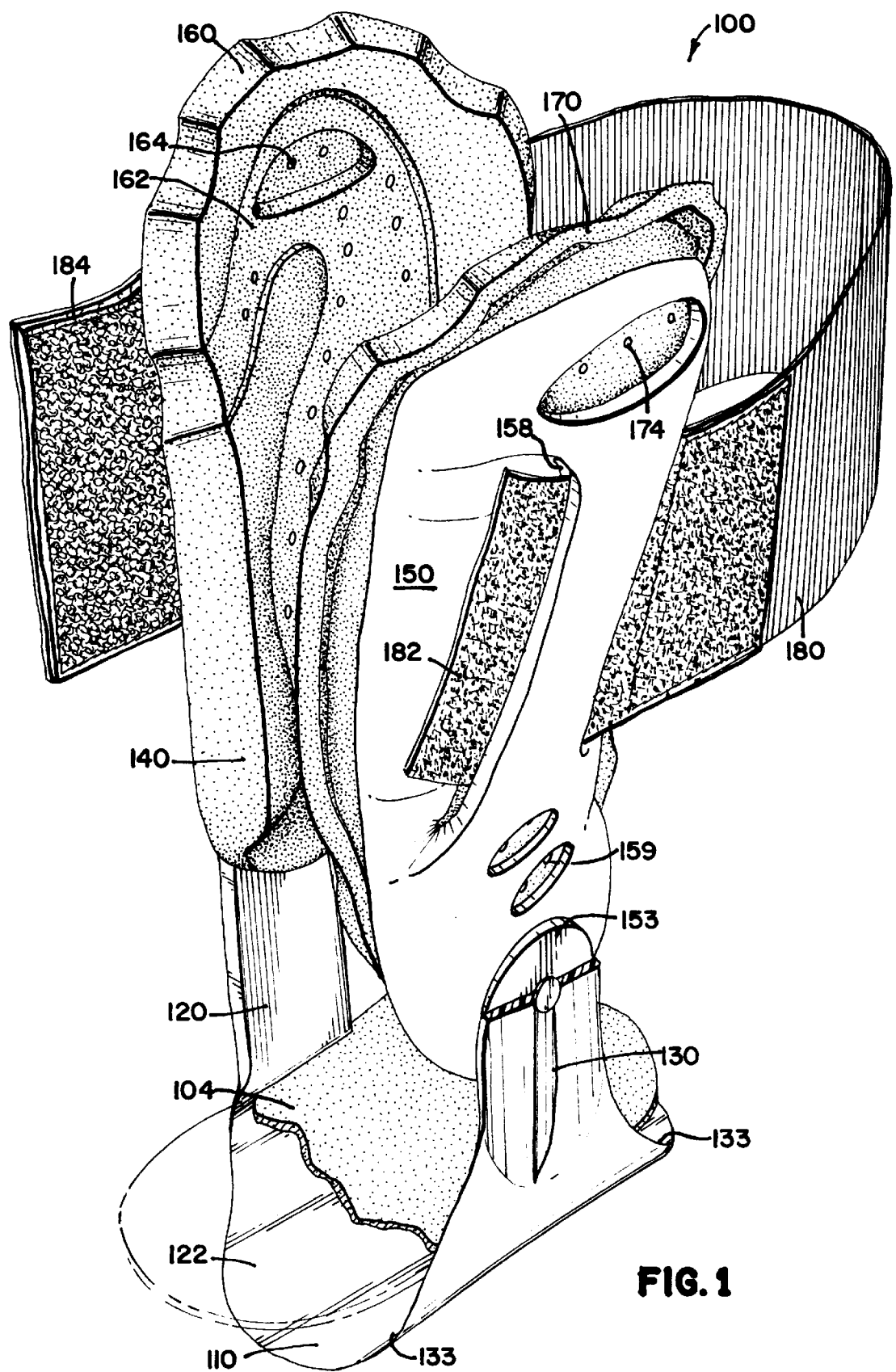
FIG. 1 is a partially sectioned, perspective view of a preferred embodiment ankle brace constructed according to the principles of the present invention.
Figure 2:
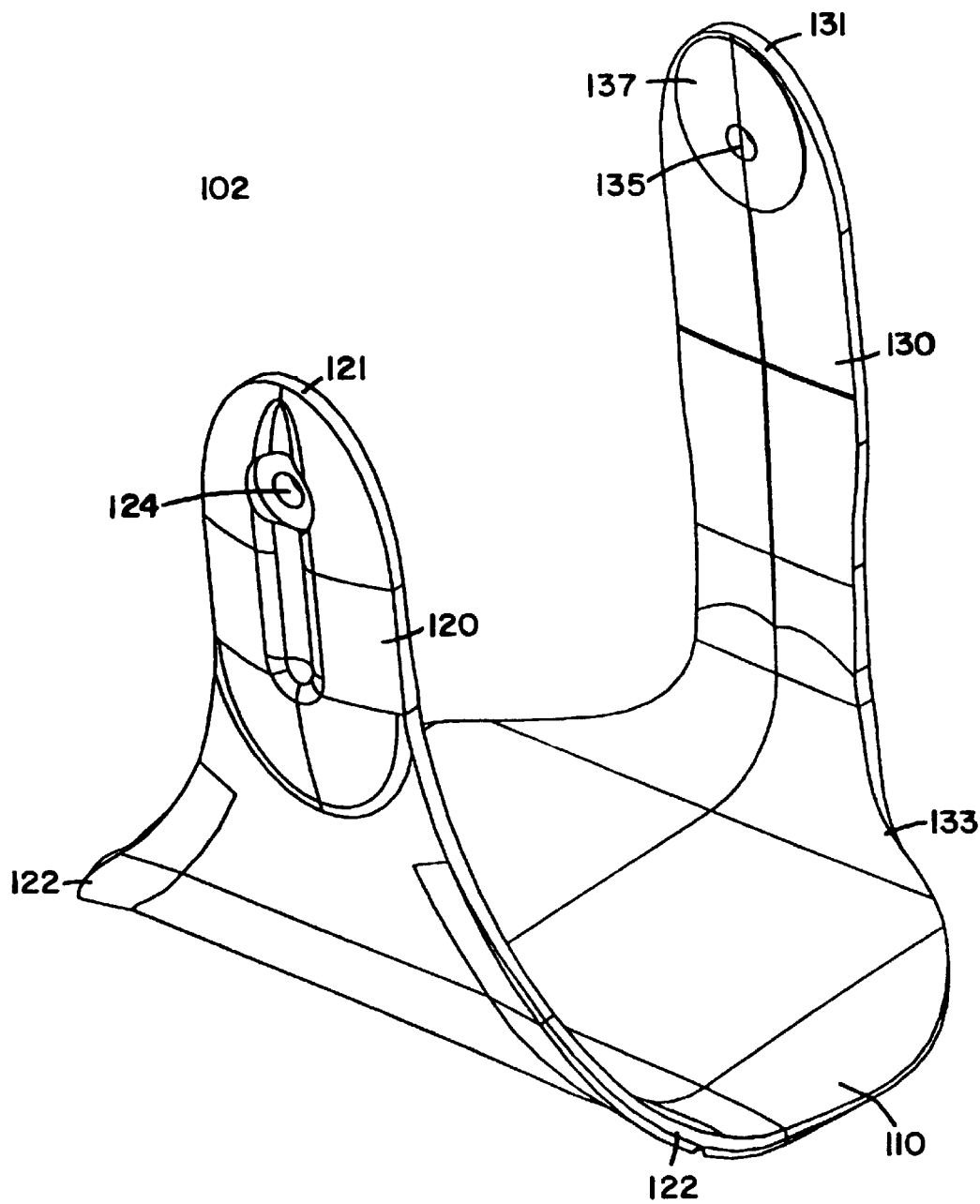
FIG. 2 is a perspective view of a lower component of the ankle brace of FIG. 1.

A preferred embodiment ankle brace constructed according to the principles of the present invention is designated as 100 in FIG. 1. The ankle brace 100 generally includes a foot plate 110; a lateral upright 120; a medial upright 130; a lateral side panel 140; a medial panel 150; a lateral pad 160; a medial pad 170; and a strap 180. Where dimensions or ranges of dimensions are given, it is to be understood that different size feet will require different size braces, and thus, the scope of the present invention is not limited to any particular size or dimension.

The foot plate 110, the lateral upright 120, and the medial upright 130 are integral portions of a plastic member 102 which may be described as generally U-shaped. Each of the foot plate 110, the lateral upright 120, and the medial upright 130 has a mean thickness which falls within the range of one-eighth of an inch to one-twelfth of an inch, and which may be generally described as approximately one-tenth of an inch. The distance A between the lateral upright 120 and the medial upright 130 falls within the range of two and one-half inches to three inches, and may be generally described as approximately two and three-quarter inches.

The configuration of the foot plate 110 may be described with reference to FIGS. 4–6. The foot plate 110 is generally flat and may be said to be adapted to lie beneath a person's foot. The foot plate 110 is bounded by a relatively longer, lateral side 112, which is disposed opposite and extends parallel to a relatively shorter, medial side 113. The length B of the lateral side 112 (shown in FIG. 4) falls within the range of three and three-quarters inches to four and one-half inches, and may be generally described as approximately four and one-eighth inches. The length C of the medial side 113 (shown in FIG. 5) falls within the range of one inch and one and one-quarter inches, and may be generally be described as approximately one inch.

Relatively long distal edges 115 and 116 diverge from opposite ends of the medial side 113 and then curve into relatively short distal edges 117 and 118, which converge toward opposite ends of the lateral side 112. The foot plate 110 is symmetrical about a plane of symmetry Z which extends perpendicular to the planes in which FIGS. 4–6 are depicted and perpendicularly between the lateral side 112 and the medial side 113. As a result of this symmetrical construction, the ankle brace 100 is reversible—suitable for use on either a person's right ankle or a person's left ankle.

As shown in FIG. 1, a pad 104 is adhesively secured to the top of the foot plate 110. The pad provides a cushion between the foot and the foot plate 110. The cushion may be made from any suitable material, such as an EVA foam. Cleats or nubs 119 protrude downward from the foot plate 110 to help hold the foot plate 110 in place relative to the sole 90 (shown in FIGS. 4–5) of a shoe into which the foot plate may be inserted. In other words, the cleats 119 may be said to provide a means for biasing the foot plate 110 against movement relative to the sole of a shoe. As a result of the cleats 119, the brace 100, the shoe, and the person's ankle tend to move together or not at all, thereby reducing the likelihood of spraining the ankle or aggravating an existing injury. Those skilled in the art will recognize that various alternative biasing means may be used in place of the cleats 119. For example, zigzagging ridges or hook and loop type fasteners could be disposed on the bottom side of the foot plate 110 to discourage movement of the foot plate 110 relative to the sole of a shoe.

The lateral upright 120 extends generally perpendicularly upward from the foot plate 110. The lateral upright 120 extends from a lower end, which is integrally joined to the lateral side 112 of the foot plate 110, to an upper, distal end 121. The lateral upright 120 widens from its upper end 121 to its lower end to meet the relatively longer lateral side 112. Proximate the juncture therebetween, portions of the foot plate 110 and the lateral upright 120 curve or flange outward and join to define a hyperbolic paraboloid in the region designated as 122. The term "outward" is intended to mean downward with respect to the foot plate portion, and away from the opposite upright with respect to the upright portion. This contouring or "flanging" at each end of the juncture between the foot plate 110 and the lateral upright 120 significantly enhances the structural integrity of the member 102, and also, tends to conform to the shapes of both the exterior of a person's foot and the interior of a person's shoe.

The large two way radius of the hyperbolic paraboloid of the lateral side supports the outside of the foot and ankle in their natural position and traps the lower foot in this position which significantly restricts the ankle from rolling or bending outward, thereby providing increased lateral support and inversion restriction.

A hole 124 extends through the lateral upright 120, proximate the upper end 121. The hole 124 extends through an inwardly facing, generally oval bearing surface 127 on the upright 120. The term "inwardly facing" is intended to mean facing toward the opposite upright.

A hole of comparable size extends through the lateral side panel 140, proximate its lower end. The hole extends through an outwardly facing, generally oval bearing surface on the side panel 140 (designated 143 in FIG. 1). The term "outwardly facing" is intended to mean facing away from the opposite upright. The lateral side panel 140 is sized and configured to support the lateral side or outside of a person's lower leg. The lateral side panel 140 is rotatably connected to the lateral upright 120 by aligning the holes through each and then inserting a rivet or other suitable fastener through the aligned holes and securing it in place. When the lateral side panel 140 is rotated to a position extending generally perpendicular to the foot plate 110, the abutting bearing surfaces 143 and 127 on the side panel 140 and the upright 120 substantially align with one another. The oval configuration of the bearing surfaces tends to increase inversion restriction.

The medial upright 130 extends generally perpendicularly upward from the foot plate 110. The medial upright 120 extends from a lower end, which is integrally joined to the medial side 113 of the foot plate 110, to an upper, distal end 131. The medial upright 120 has a substantially constant width due to the relatively short length of the medial side 113.

As on the lateral side 112, the ends of the juncture between the foot plate 110 and the medial upright 130 curve or flange outward to define a hyperbolic paraboloid in the region designated as 133.

A hole 135 extends through the medial upright 130, proximate the upper end 131. The hole 135 extends through an inwardly facing, generally oval bearing surface 137 on the upright 130. A hole of comparable size extends through the medial side panel 150, proximate its lower end. As shown in FIG. 1, the side panel 150 is "behind" the pad 170. The hole extends through an outwardly facing, generally oval bearing surface on the side panel 150. The medial side panel 150 is sized and configured to support the medial side or inside of a person's lower leg. The medial side panel 150 is rotatably connected to the medial upright 130 in the same manner as discussed above with respect to the lateral side panel 140. When the medial side panel 150 is rotated to a position extending generally perpendicular to the foot plate 110, the abutting bearing surfaces on the side panel 150 and the upright 130 substantially align with one another.

The lateral pad 160 is secured inside the lateral side panel 140 by hook and loop fasteners or other suitable means, and the medial pad 170 is secured inside the medial side panel 150 in like fashion. The term "inside" is intended to mean between the panels 140 and 150. The pads 160 and 170 are made of EVA copolymer foam or some other suitable material. They are first molded in a flat configuration and then disposed in a cooling fixture which shapes them to rest comfortably against respective sides of a person's lower leg. Accordingly, the side panels 140 and 150 have a concave shape to substantially conform to the pads 160 and 170. The side panel 140 being of similar shape as panel 150 except being slightly longer due to the shorter length of medial upright 120.

The strap 180 is wrapped around the side panels 140 and 150 and pulled tight to clamp or squeeze a person's lower leg therebetween. In particular, a first end 184 is attached to adhesive hook on the medial side panel 150 and a second, opposite end 182 is inserted through parallel slots 148 in the lateral side panel 140. The two ends 182 and 184 are then secured to one another by hook and loop fasteners or other suitable means.

Ventilation holes 149 extend through the lateral side panel 140, and comparable ventilation holes extend through the lateral side panel 150. A generally S-shaped recess or shallow channel (one of which is designated as 172) is provided in the inwardly facing side of each pad 160 and 170 to help conduct heat out of the brace 100. Each recess extends from an upper edge along one side of a respective pad to a lower edge along an opposite side of a respective pad. Also, ventilation holes 174 and 164 extend through the pads 170 and 160 in the regions of the recesses, and at some of these holes 164 and 174 align with the openings through the side panels 140 and 150.

Figure 3:
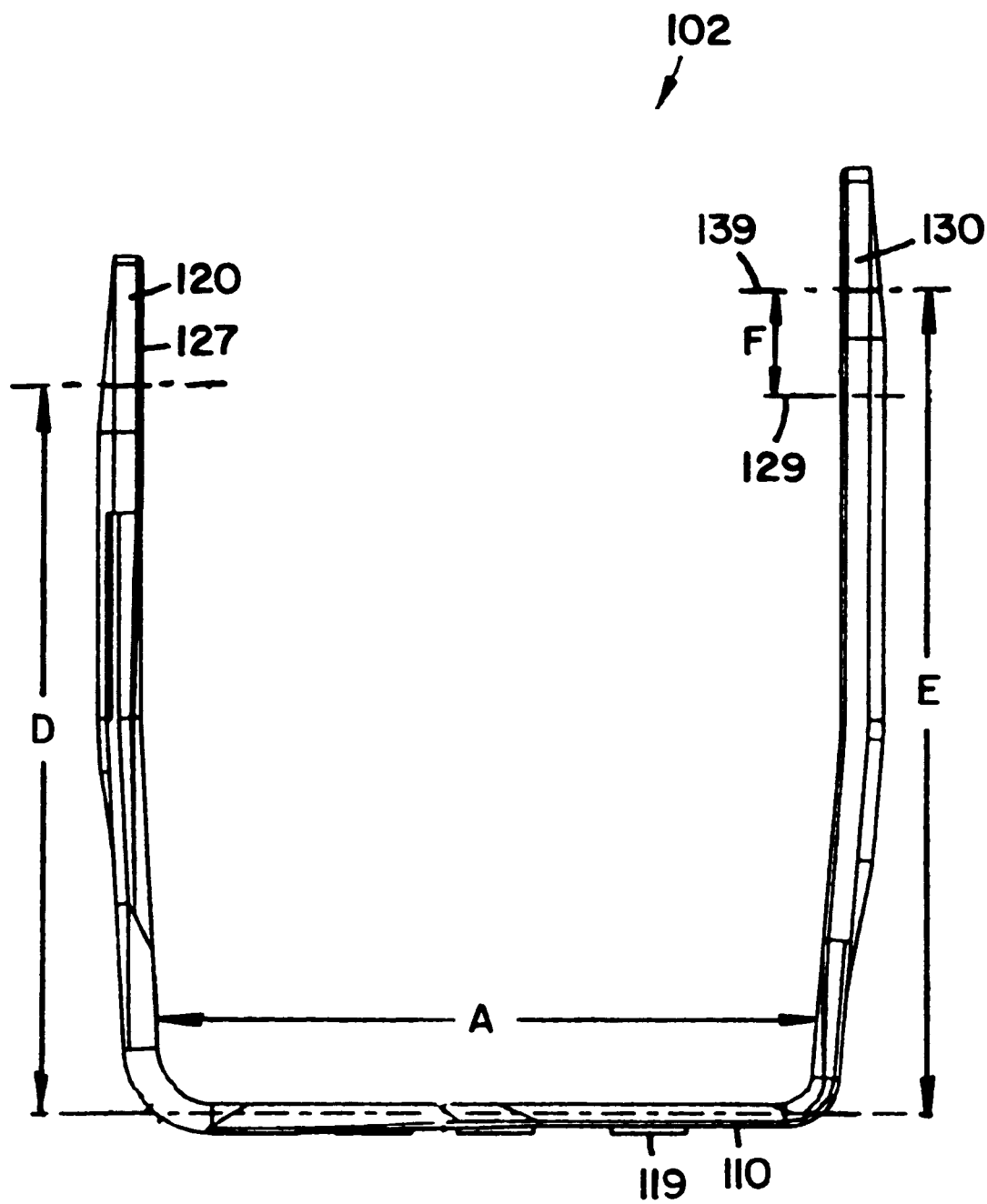
FIG. 3 is an end view of the component of FIG. 2.
Figure 4:
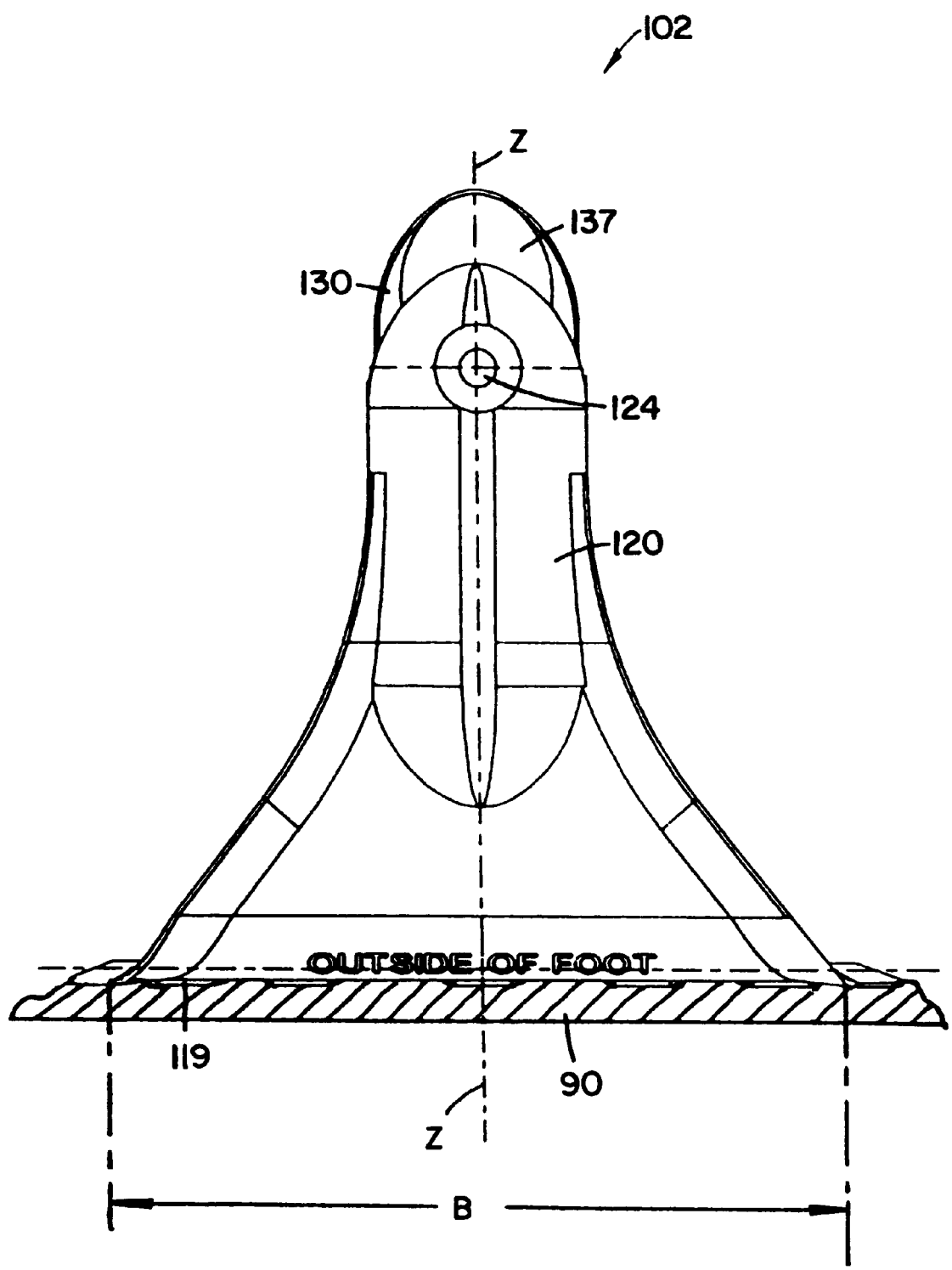
FIG. 4 is a side view of the component of FIG. 2.
Figure 5:
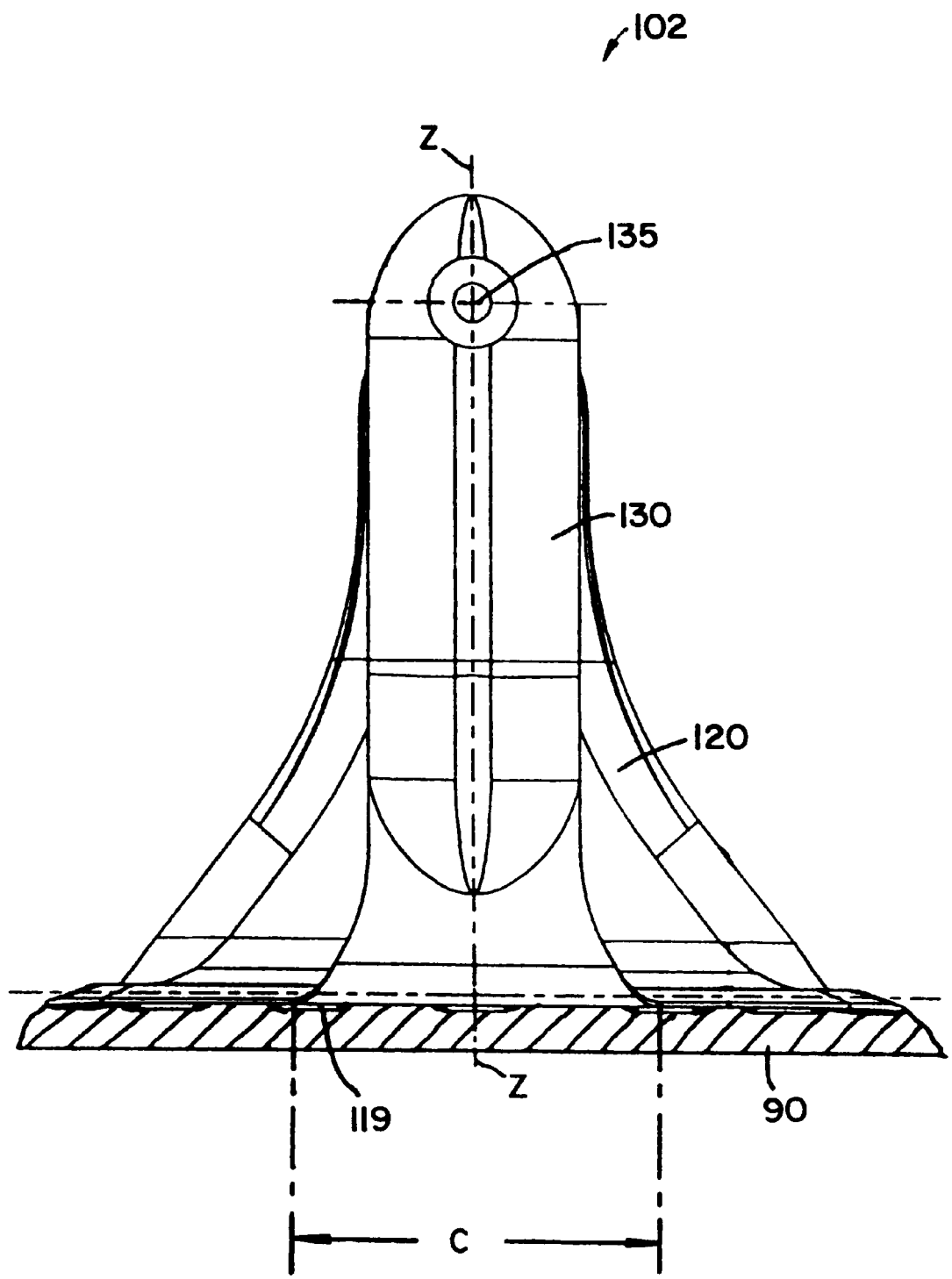
FIG. 5 is an opposite side view of the component of FIG. 2.
Figure 6:
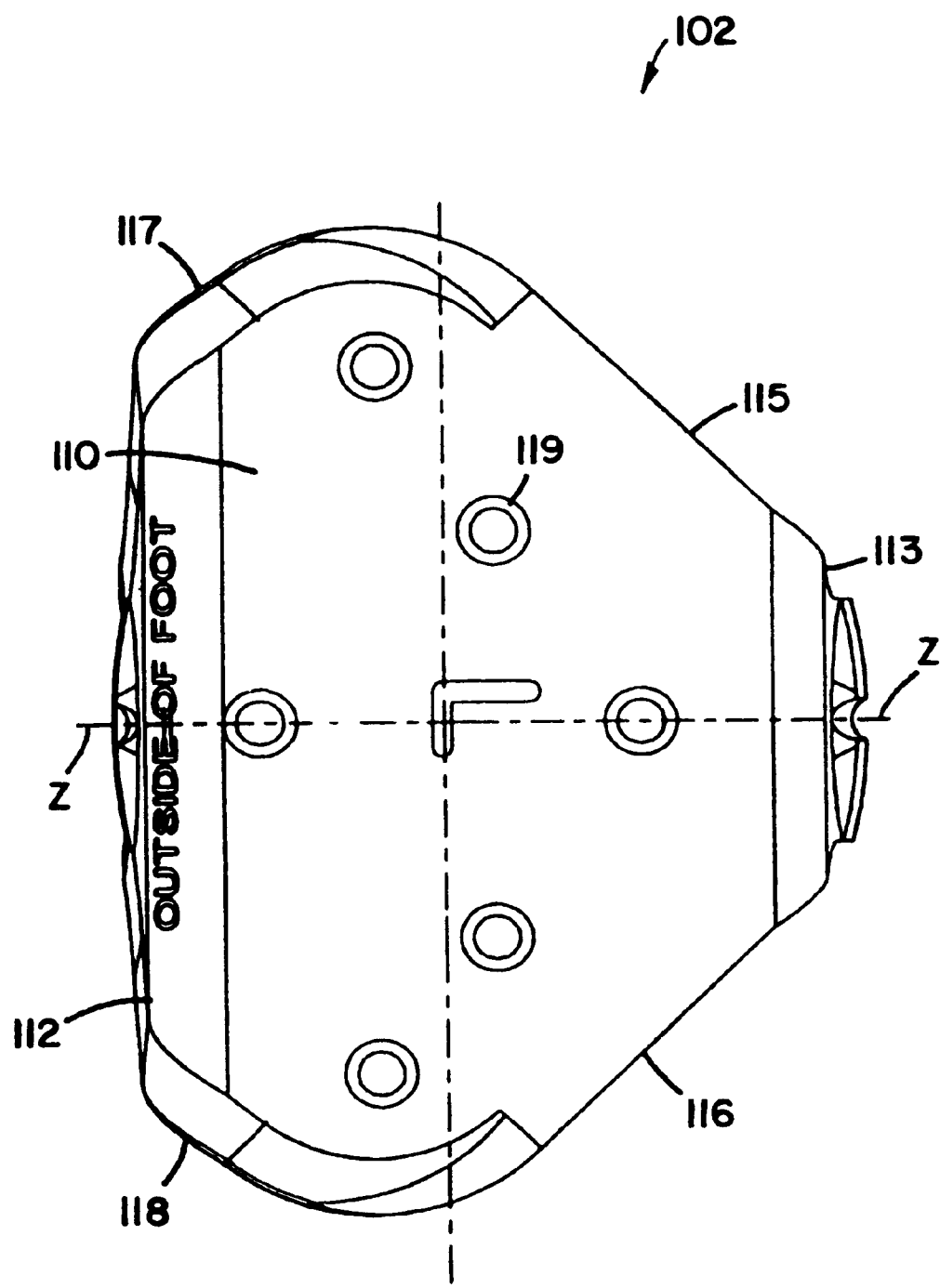
FIG. 6 is a bottom view of the component of FIG. 2.
Figure 7:
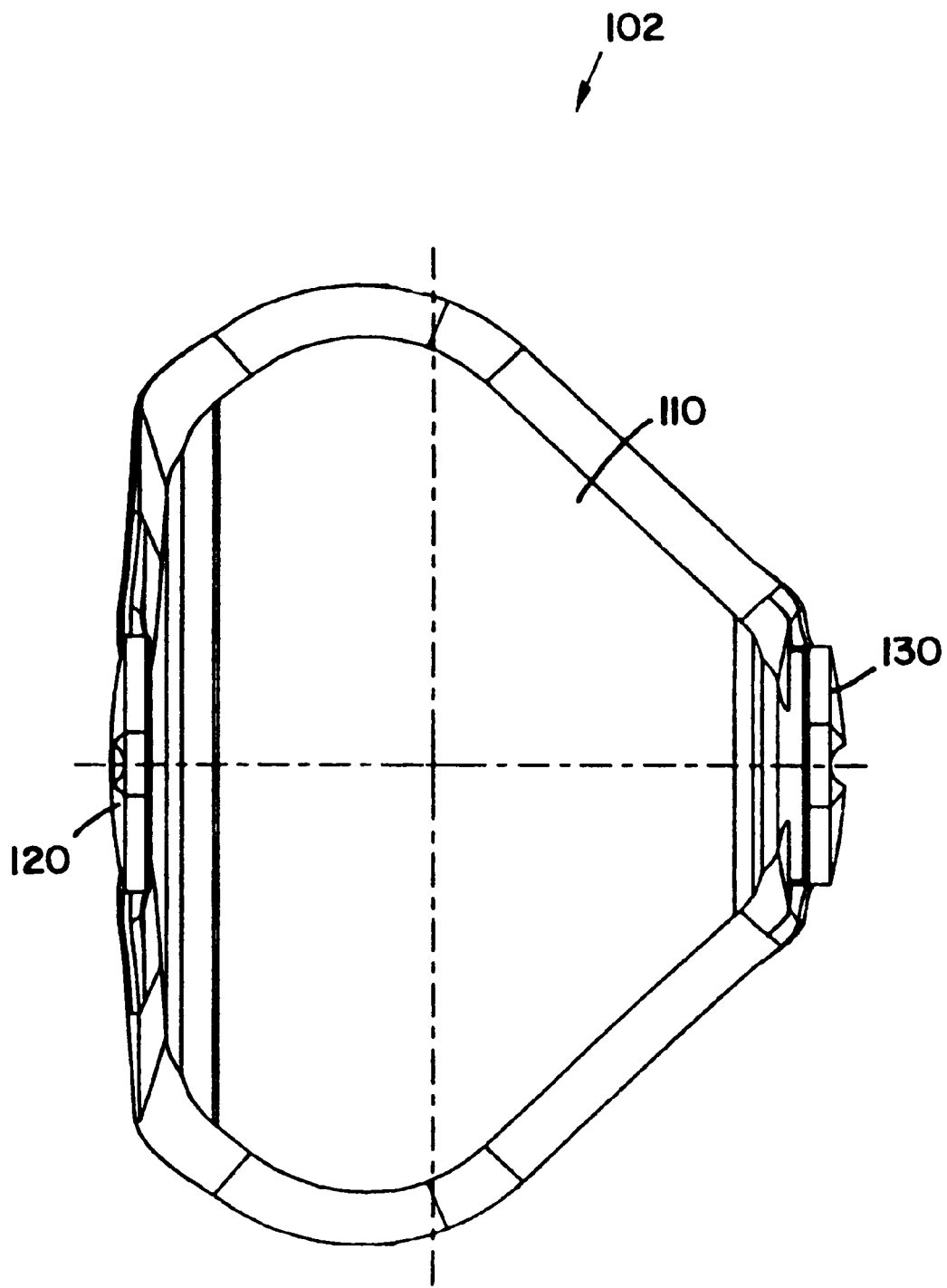
FIG. 7 is a top view of the component of FIG. 2.

As shown in FIGS. 3–6, the pivot point or rotational axis 139 for the medial side panel 150 and the pivot point or rotational axis 129 for the lateral side panel 140 lie within the plane of symmetry Z. However, as shown in FIGS. 3–5, the distance E between the foot plate 110 and the axis 139 is greater than the distance D between the foot plate 110 and the axis 129.

In particular, the distance E falls within the range of three inches and three and three-quarters inches, and may be generally described as approximately three and three-eighths inches; and the distance D falls within the range of two and three-quarters inches and three and three-eighths inches, and may be generally described as approximately three inches. Thus, the extent of offset F between the two axes 139 and 129 may be generally described as approximately three-eighths of an inch, as measured perpendicular to the foot panel 110. The offset F is intended to enhance the ergonomic fit of the ankle brace 100.

In a preferred embodiment, the lateral side has a longer length and substantially increases the surface area below the pivot point which results in increased positive contact with the upright and therefore significantly decreases the possibility of the side panel bending out which increases lateral support and inversion restriction.

The present invention has been described with reference to the preferred embodiment and a particular application. However, this description may lead others skilled in the art to recognize other embodiments and/or applications which nonetheless embody the essence of the present invention. Accordingly, the scope of the present invention is to be limited only to the extent of the following claims.

What is claimed is:

1. An ankle brace of the type which is disposed both about a person's lower leg and beneath the person's foot, the improvement comprising:
   a foot plate adapted to lie beneath the person's foot, the foot plate having a lateral side and an opposite, medial side, wherein the lateral side is at least twice as long as the medial side, and the foot plate is symmetrical about a plane of symmetry extending perpendicularly through the lateral side and the medial side.

2. The ankle brace of claim 1, the improvement further comprising:
   a lateral upright extending upward from the lateral side of the foot plate and providing a first pivot point which lies within the plane of symmetry; and
   a medial upright extending upward from the medial side of the foot plate and providing a second pivot point which lies within the plane of symmetry.

3. The ankle brace of claim 2, wherein the second pivot axis is offset approximately three-eighths of an inch farther above the first pivot axis, as measured in a direction normal to the foot plate.

4. The ankle brace of claim 3, the improvement further comprising:
   a lateral side panel rotatably connected to the lateral upright at the first pivot point; and
   a medial side panel rotatably connected to the medial upright at the second pivot point.

5. The ankle brace of claim 2, the improvement further comprising:
   a lateral side panel rotatably connected to the lateral upright at the first pivot point; and
   a medial side panel rotatably connected to the medial upright at the second pivot point.

6. The ankle brace of claim 1, the improvement further comprising:
   a lateral upright extending upward from the lateral side of the foot plate, wherein edge portions of the foot plate and the lateral upright proximate their juncture with one another are outwardly curved.

7. The ankle brace of claim 1, the improvement further comprising:
   cleats protruding downward from a downwardly facing surface on the foot plate.

8. An ankle brace of the type which is disposed both about a person's lower leg and beneath the person's foot, comprising:
   a foot plate adapted to lie beneath the person's foot, the foot plate having a lateral side and a medial side;
   a lateral upright extending upward from the lateral side of the foot plate, wherein edge portions of the foot plate and the lateral upright proximate their juncture with one another are outwardly curved; and
   a medial upright extending upward from the medial side of the foot plate.

9. The ankle brace of claim 8, wherein said edge portions of the foot plate and the lateral upright cooperate to define a hyperbolic paraboloid.

10. The ankle brace of claim 8, wherein cleats protrude downward from a downwardly facing surface on the foot plate.

11. An ankle brace of the type which is disposed both about a person's lower leg and beneath the person's foot, and which may be worn inside a shoe, the improvement comprising:
    said ankle brace having a foot plate adapted to lie beneath the person's foot, said foot plate having cleats protruding downward, away from the person's foot, wherein said cleats are configured to lie within the shoe for retarding slippage of said foot plate relative to the shoe.

12. The ankle brace of claim 11, wherein the foot plate is made of plastic having a mean thickness of approximately one-tenth of an inch, and the foot plate is an integral portion of a generally U-shaped member.

13. An ankle brace of the type which is disposed both about a person's lower leg and beneath the person's foot, comprising:

a foot plate adapted to lie beneath the person's foot, the foot plate having a lateral side and an opposite, medial side;

a lateral upright extending upward from the lateral side of the foot plate to an upper end having a flat, inwardly facing bearing surface;

a lateral panel rotatably mounted to the lateral upright, proximate the upper end, the lateral panel being configured to curve about the lateral side of the person's lower leg and having a flat, oval-shaped surface which abuts the bearing surface on the lateral upright;

a medial upright extending upward from the medial side of the foot plate to an upper end having a flat, inwardly facing bearing surface; and a medial panel rotatably mounted to the medial upright, proximate the upper end, the medial panel being configured to curve about the medial side of the person's lower leg and having a flat, oval-shaped surface which abuts the bearing surface on the medial upright.

14. The ankle brace of claim 13, further comprising a lateral foam pad mounted inside the lateral panel, and a medial foam pad mounted inside the medial panel, wherein ventilation holes extend through each said pad.

15. The ankle brace of claim 14, wherein a generally S-shaped recess is formed into an inwardly facing surface on each said pad.

16. The ankle brace of claim 14, wherein ventilation holes extend through each said panel and align with at least some of the ventilation holes extending through a respective pad.

17. The ankle brace of claim 14, wherein each said bearing surface is oval-shaped.

18. An ankle brace of the type which is disposed both about a person's lower leg and beneath the person's foot, comprising:

a foot plate adapted to lie beneath the person's foot, the foot plate having a lateral side and an opposite, relatively shorter, medial side;

a lateral upright extending generally perpendicularly upward from the lateral side of the foot plate to an upper end;

a lateral panel rotatably mounted to the lateral upright proximate the upper end thereof;

a medial upright extending generally perpendicularly upward from the medial side of the foot plate to an upper end; and a medial panel rotatably mounted to the upper end of the medial upright proximate the upper end thereof, wherein the ankle brace is configured to be reversible, whereby the foot plate, each said upright, and each said panel occupies a like relative position on either of a person's feet.

19. An ankle brace of the type which is disposed both about a person's lower leg and beneath the person's foot, comprising:

a foot plate adopted to lie beneath the person's foot, the foot plate having a lateral side and an opposite, relatively shorter medial side, wherein a plane of symmetry extends through the footplate, perpendicular to the lateral side and the medial side;

a lateral upright extending upward from the lateral side of the foot plate to an upper end;

a lateral panel rotatably mounted to the lateral upright proximate the upper end thereof;

a medical upright extending upward from the medial side of the foot plate to an upper end; and a medical panel rotatably mounted to the upper end of the medical upright proximate the upper end thereof, wherein the ankle brace is configured to be reversible, and each said panel occupies a like relative position on either of a person's feet.

20. The ankle brace of claim 19, wherein the lateral upright and the lateral panel define a first rotational axis, and the medial upright and the medial panel define a second rotational axis, and the second rotational axis is offset approximately three-eighths of an inch above the first rotational axis, as measured in a direction normal to the foot plate.

21. The ankle brace of claim 18, further comprising a lateral foam pad mounted inside the lateral panel, and a medial foam pad mounted inside the medial panel, wherein a ventilation channel extends along an interior side of each said pad, and ventilation holes extend through each said pad within a respective channel, and at least some of the ventilation holes through each said pad align with at least one opening through a respective panel.

* * * * *